United States Patent

Coffee

[11] Patent Number: 6,105,877
[45] Date of Patent: *Aug. 22, 2000

[54] DISPENSING DEVICE

[75] Inventor: Ronald Alan Coffee, Haslemere, United Kingdom

[73] Assignee: Electrosols Ltd., Surrey, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/835,676

[22] Filed: Apr. 10, 1997

Related U.S. Application Data

[63] Continuation of application No. 08/456,432, filed as application No. PCT/GB30/02443, Nov. 26, 1993, abandoned.

[30] Foreign Application Priority Data

Dec. 1, 1992 [GB] United Kingdom ............ 9225098

[51] Int. Cl.⁷ ........................................... B05B 5/00
[52] U.S. Cl. .................. 239/3; 239/690; 239/696; 239/708; 128/204.21
[58] Field of Search ................... 239/690, 695, 239/696, 708, 102.2, 3; 361/227, 228; 128/203.12, 200.14, 204.13, 204.21

[56] References Cited

U.S. PATENT DOCUMENTS

| | | | |
|---|---|---|---|
| 2,723,646 | 11/1955 | Ransburg | 118/51 |
| 2,945,443 | 7/1960 | Aver et al. | 103/1 |
| 3,131,131 | 4/1964 | Wehner | 195/51 |
| 4,198,781 | 4/1980 | Dykes | 47/1.3 |
| 4,380,786 | 4/1983 | Kelly | 361/228 |
| 4,703,891 | 11/1987 | Jackson et al. | 239/171 |
| 4,788,016 | 11/1988 | Colclough et al. | |
| 4,830,872 | 5/1989 | Grenfell | 427/30 |
| 5,115,971 | 5/1992 | Greenspan et al. | 239/3 |
| 5,180,288 | 1/1993 | Richter et al. | 417/48 |
| 5,402,945 | 4/1995 | Swanson | 239/706 |
| 5,655,517 | 8/1997 | Coffee | 128/203.12 |

FOREIGN PATENT DOCUMENTS

| | | |
|---|---|---|
| 0 120 633 A2 | 10/1984 | European Pat. Off. . |
| 0 102 713 B1 | 9/1987 | European Pat. Off. . |
| 0 243 031 A1 | 10/1987 | European Pat. Off. . |
| 195704 | 12/1980 | New Zealand . |
| 198774 | 10/1981 | New Zealand . |
| 191545 | 6/1984 | New Zealand . |
| 2 128 900 | 5/1984 | United Kingdom . |
| 2 201 873 | 9/1988 | United Kingdom . |

OTHER PUBLICATIONS

Article entitled: *Electro–osmosis Controls Fluid in Novel Transducer Concept by Product Engineering*, dated Jul. 4, 1970 authored by: Ray Lewis, Cleveland, pp. 71–72.

Article entitled: *Electrodynamic Crop Spraying*, dated 1981; authored by: R. A. Coffee; Reprinted from Outlook on Agriculture vol. 10, No. 7, 1981; includes excerpt pp. 350–356.

*Primary Examiner*—Patrick Brinson
*Assistant Examiner*—Lisa Ann Douglas
*Attorney, Agent, or Firm*—Cobrin & Gittes

[57] ABSTRACT

A device for comminuting liquid has a liquid supply with first and second outlets, a first electrohydrodynamic comminuter for subjecting liquid issuing from the first outlet to an electrical potential to cause the liquid to be commrinuted to form a comminution of one polarity and a second electrohydrodynamic comminuter for subjecting liquid issuing from the second outlet to an electrical potential to cause liquid to be commninuted to form a comminution of the opposite polarity. The first and second electrohydrodynamic comminuters are arranged so as to cause substantial admixing of two opposite polarity comminutions.

44 Claims, 4 Drawing Sheets

DISPENSING DEVICE

This application is a continuation of U.S. Application, Ser. No. 08/456,432 filed on Jun. 1, 1995, now abandoned which is a 371 of PCT/GB30/02443, filed Nov. 26, 1993.

The invention relates to a dispensing device for comnminuting a liquid, means for supplying liquid for use in such device and the use of such a device, in particular, in medicine.

Dispensing devices are known which produce a finely divided spray of liquid droplets by electrostatic means(more properly referred to as 'electrohydrodynamic' means). Electrohydrodynamic sprayers have found use in many areas of industry, especially in agriculture for crop spraying, paint spraying in the automotive industry and also in medicine for the administration of medicaments by inhalation.

The droplet spray in such devices is generated by applying an electric field to a liquid located at a spray head or spray edge. The potential of the electric field is sufficiently high to provide comminution of electrically charged liquid droplets from the spray head. The electrical charge on the droplets prevents them from coagulating via mutual repulsion.

United Kingdom patent number 1569707 describes an electrohydrodynamic spray device principally for use in crop spraying. An stated essential component of the GB 1569707 spray device is a field intensifying electrode, cited adjacent the spray head and maintained at the same potential as the spray head. The field intensifying electrode is not supplied with liquid. In use it is stated to reduce the incidence of corona discharge which interfere with spray production and thereby allows lower electric field strengths to be used during spray generation.

U.S. Pat. No. 4,703,891 describes an crop spraying apparatus fi spraying liquids from a vehicle such as an aircraft or other airborne vehicle, having least two sprayheads arranged to produce spray of positive charge at one sprayhead and negative charge at the other. The resulting charged sprays are then applied to the relevant crops.

In many circumstances it is desirable to partially or wholly remove the elect charge from droplet sprays produced by electrohydrodynamic comminution devices in a controlled manner. To date the principal method used to effect comminution discharge has required the use of a discharging electrode having a sharp or pointed edge and located downstream from the spray head. The discharging electrode produces a cloud of charged ions from the surrounding air having an opposite electrical charge of equal magnitude to that on the comrninuted liquid spray. In us the ion cloud is attracted towards, collides with and thereby neutalizes the liquid spray.

United Kingdom patent number 2018627B discloses an electrohydrodynamic spray device wherein the electric charge on the droplet spray is fully or partially removed by means of a discharge electrode. The UK 2018627B device is stated to provide discharged or partially discharged sprays for crop spraying purposes. European Patent number 0234842 discloses an electrohydrodynamic inhaler wherein the spray of charged droplets is similarly discharged by means of a discharge electrode. The droplets are discharged in order to facilitate droplet deposition into the respiratory tract as otherwise the electrically charged droplets would deposit onto the mouth and throat of the user.

A particular problem associated with the use of the sharp discharge electrode is that the highly mobile ion cloud from the discharge electrode often interferes with the comminution of the liquid spray. The inhaler device of EP 0234842 attempts to ameliorate the effects of the ion cloud at the spray head by using a neutral shield electrode located close to the spray head.

It is a primary feature of the present invention that a device for comminuting a liquid is provided, which comminutes the liquid by electrohydrodynamic means and which produces a partially or fully electrically discharged comminution without the need for the sharp discharge electrode described above. The present device does not have the problems associated with the discharge electrode and hence it does not require the use of a neutral shield electrode.

Accordingly, there is provided a device for comminuting a liquid, which comprises at least two electrohydrodynamic comminution means arranged so that in use comminutions of opposing polarity are formed which are substantially admixed after formation.

The electrohydrodynamic comminution means may be any conventional electrohydrodynamic comminution means, for example those described in the above mentioned patent specifications.

Suitably, each comminution means comprises a comminution site, generally being a surface or edge, from which the liquid comminution is produced.

A preferred comminution surface or edge is provided by a thin capillary tube, a nozzle or a slot defined by two parallel plates. However any comminution surface or edge described in the above mentioned patent specifications may be used.

The device generally comprises an even number of comminution means but this is not essential, the key factors are that at least two of the comminution means provide comminutions of opposing polarity and that the comminutions produced are arranged to substantially admix.

Suitably, the device comprises 2,4 or 6 comminution means, however higher numbers can be used as required An example of a device is that which has 2 comminution means. An example of a device is that which has 6 comminution means.

Suitably, each comminution means comprises a means for supplying liquid to the comminution site.

Appropriate means for supplying liquid to the comminution site include mechanical, electrical or electronic powered means such as pumps which are capable of providing the required flow rate of liquid to the cornminution site.

The comminution means of the invention can be used with a large range of flow rates, but generally operates with flow rates in the range of between 0.1 to 500 $\mu$l per second, such as 0.5 to 5 $\mu$L per second, especially for inhaled administration, or 10 to 200 $\mu$L per second, especially for agricultural use.

A suitable means for supplying the liquid includes a syringe pump or an electrically powered pump as described in EP 0029301.

It will be appreciated from the foregoing that the comminution means generally comprises a comminution site, a means for supplying a liquid to the comminution site and a means for electrically charging the comminution site to an electric potential sufficient to comminute the liquid in use.

Accordingly, in one particular aspect of the invention there is provided a device for comminuting a liquid, which comprises at least two electrohydrodynamic comminution means each comprising a comminution site, a means for supplying a liquid to the comminution site and a means for electrically charging the comminution site to an electric potential sufficient to comminute the liquid in use, wherein the comminution means are arranged so that in use comminutions of opposing polarity are formed which are then substantially admixed.

Suitably, each comminution means comprises a means for electrically charging the said comminution site to a potential sufficient to provide comminution of the liquid, the potential usually being of the order of 1–20 kilovolts.

The means for electrically charging the said comminution site, such as a surface or edge, may be provided by any conventional high voltage generator having the appropriate output, one particularly convenient generator being a piezoelectric generator.

The piezoelectric material for the generator may be chosen from several types, such as barium titanate ceramic, or pvdf polymers, which generate significant high-voltage electric charge displacement upon being pressurized. The choice and capacity may be so chosen as to offer control of the degree of pumping and/or atomization when operated.

The required voltage for use is provided when the piezoelectric generators are squeezed, and again (with opposite polarity) when the piezoelectric generators are released from pressure.

The arrangement by which the comminutions are admixed enables the net charge on the admixed comminution to be either essentially neutral, positive or negative. Generally, the residual positive or negative charges are less than the positive or negative charge on any of the premixed comminutions.

The net residual charge on the admixed comminution may be fixed for any given device or the arrangement may be such that the net residual charge on the admixed comminution may be regulated in a controlled manner. Thus the device of the invention optionally comprises a means for regulating the electrical charge on a comminution produced from any of the cormminution means prior to admixture.

Suitable means for regulating the electrical charge on a comminution may be provided by a variety of methods, such as by incorporating a means for regulating the charging means so as to provide variable voltage output andlor a means for regulating the means for supplying a liquid to the comminution site so as to vary the liquid flow rate to the comminution site.

Suitable arrangements of the comminution means which enable the comminutions produced to be admixed includes any arrangement wherein the comminution means are relatively located so as to enable the comminutions to substantially admix. Favourably, the comminution means are arranged so that the comminutions produced are directed to converge into a mixing zone. For example, when the device comprises two comminution means they may be angled towards each other so as produce comminutions which converge into the mixing zone. Or when the device comprises three or more comminution means, they may be arranged so that the comminutions are directed to converge radially into the mixing zone. Alternatively, the relative location of the comminution means may be arranged such that the mutual attraction of the comminutions produced is sufficient to allow substantial admixing, for example they may be in a mutually parallel manner.

It is envisaged that a liquid supply means may supply one or more of the comminution means of the invention.

Alternatively, a liquid supply means may supply only one comminution means.

From the foregoing it will be appreciated that it is an aspect of the present invention that comminuted sprays from different liquids may be mixed as required. Such liquids may be capable of providing a new product on admixture or they may comprise components which are so capable. The device may also be used to mix two liquids which are reactive components of a rapid chemical reaction. In each case the mixed droplets may then be applied as a spray, with a charge-to-mass ratio on the droplets that will be the residual after the two opposing charges have been used to coalesce the liquids.

Similarly, the present device may be used to mix components which are incompatible one with the other and which therefore are advantageously admixed at the point of use.

Suitable liquids include liquids comprising components useful for human or animal health care, such as medicaments for pharmaceutical or public health care use or medically useful compounds such as anesthetics.

Suitable liquids include liquids comprising components for agricultural use such as pesticides or biocides.

Suitable liquids include liquid cosmetic formulations.

Other suitable liquids include paints and inks. Also included are liquids for providing aromas.

Preferred liquids are pharmaceutically active liquids.

The comminution means of the dispenser provides liquid droplets within the range of from about 0.1 to about 500 microns in diameter: More usually from 0.1 to 200 microns, such as 1.0 to 200 microns: Examples include droplets within the range of 5.0 to 100, 0.1 to 25, 0.5 to 10 or 10 to 20 microns. A favoured range for inhaled administration is 0.1 to 25 or 0.5 to 10 microns, especially for administration to the lower respiratory tract, and 10 to 25 microns, especially for administration to the upper respiratory tract.

For a given liquid the diameter of the droplets can be controlled by varying the applied voltage and liquid flow rate using routine experimental procedures. Liquids having viscosities within the range of from 1 to 500 centipoise and resistivities in the range of from $10^2$–$10^8$ ohm m can be comminuted by the present device.

One favoured use of the device of the invention is for the dispensation of a comminuted liquid for inhalation.

Accordingly, in one preferred aspect of the invention there is provided a device for comminuting a liquid for inhalation, which comprises at least two electrohydrodynamic comminution means each comprising a comminution site, a means for supplying a liquid to the comminution site and a means for charging the comminution site to an electric potential sufficient to comminute the liquid in use, wherein the comminution means are arranged so that in use comminutions of opposing polarity are formed which are substantially admixed after formation.

The device of the invention may be adapted into any embodiment form which dispenses comminuted liquid for inhalation, for both medicinal and non-medicinal use.

Non-medicinal inhalation uses includes dispensing perfumes and aromas.

Preferably, the device is in the form of an inhaler, for the inhaled delivery of a medicament.

A preferred liquid is therefore a liquid medicament formulation adapted for inhaled administration.

Medicaments suitable for adaption for inhaled administration include those used for the treatment of disorders of the respiratory tract, such as reversible airways obstruction and asthma and those used in the treatment and/or prophylaxis of disorders associated with pulmonary hypertension and of disorders associated with right heart failure by inhaled delivery.

Since the charge-to-mass ratio of an electrohydrodynamic comminution may sometimes require optimization, to a value that may lie anywhere between the unadjusted value at the moment of comminution, and zero, the device of the invention may also be used to optimize droplet charges. For example, in order to apply a liquid containing a therapeutic agent to specific airways within a human lung, by inhalation, it would be highly beneficial if the droplet mass and charge could be independently controlled. This would give an unprecedented degree of control over the zone of deposition of the droplets within the lung.

For example in a two nozzle dispensing device, it can be arranged to have one nozzle comminuting a spray of the medicament, such as a beta-2 agonist, for example salbutamol, where the average droplet charge+/− Qa could then be accurately adjusted by arranging for deionized water to be comminuted from the second nozzle with an average charge−/+ Qb, thus the desired final value on the inhaled spray of could be Qa plus or minus Qb.

Similqrly, for example, in charged droplet spraying of crops it is sometimes highly beneficial if the droplet charge can be adjusted independently of its mass, in order to achieve penetration into dense foliage.

As indicated above, various means have been used to deliver liquid to the comminution site prior to comminution generation. Most are mechanical in nature although European Patent number 0029301 discloses a spray device incorporating a pump wherein the hydrostatic pressure is generated by an electric potential between two electrodes immersed in the feeder stream of the liquid to be sprayed. It is a further aspect of the present invention that there is provided a novel electrically powered pump, suitable for pumping liquid to the cornminution site of an electrohydrodynamic comminution device.

An important component of the dispensing devices described above is the means for supplying the liquid to the comminution site. Accordingly, in a further aspect of the present invention there is provided a pump, suitable for supplying liquid to the comminution site of a comminution means, which pump comprises an electrically insulating conduit for the liquid, the conduit enclosing an electrically insulating solid permeable to liquid, means for retaining the solid within the conduit and means for applying an electric field across the solid, so that in use, when the electric field is applied, liquid is induced to flow through the solid and hence along the conduit.

The dimensions of the conduit are not considered to be limiting to the successful operation of the invention, the essential feature being the presence of an electric field across the solid.

A suitable means for applying an electric field across the solid is provided by a pair of permeable electrodes, spaced apart along the conduit.

It is preferred if the solid substantially fills the conduit. A suitable conduit is a pipe, for example a cylindrical pipe.

Conveniently, the means for applying an electric field across the solid also acts as the retaining means for the solid in the conduit.

In one suitable form of the invention a pair of permeable electrodes are fixed apart along the conduit and the permeable solid substantially fills the space defined by the electrodes and the inner wall or walls of the conduit.

Preferably, the electrodes are flat plates shaped to retain the solid within the conduit, thus when the conduit is a pipe the electrodes are disc shaped.

The permeable electrodes are conveniently constructed from wire gauze or from electrically conducting titanium oxide.

Suitably, the liquid permeable solid is in powdered form. Suitable powdered forms include powdered ceramic, powdered silica, powdered plastic and clay.

Alternatively, the liquid permeable solid may be a fibrous solid, suitably a fibrous ceramic or polymer fibres.

In addition as an alternative to powdered or fibrous forms the electrically insulating solid may be any permeable form of ceramic, silica, plastic or clay.

The relationship between flow rate, dimensions of the conduit, applied voltage and the nature of permeable solid riay helpfully be described by the equation shown in Scheme (I) which assumes that the permeable solid is formed by a bundle of parallel capillary fibres of radius ‘r’:

Scheme (I)

$$\text{Flow rate} = \frac{n\varepsilon_T\varepsilon_O\xi\pi r^2}{\eta}\cdot\frac{V}{L}\quad \text{m/sec}$$

wherein:

n=number of capillaries of radius r,

V=applied voltage;

L=distance between electrodes;

$\xi$=Zeta potential;

$\epsilon_r$=relative permittivity;

$\epsilon_o$=permittivity of free space; and $\eta$=viscosity of the liquid.

Although Scheme (I) is considered to be useful for describing the theoretical basis for the pump of the present invention, the invention is not considered to be limited by the relationship set out in Scheme (I).

In a preferred form, when used to supply a liquid formulation in the dispensing device of the invention, the pump comprises an electrically insulating tube, a pair of electrodes permeable to liquid and fixed apart along the tube and a powdered solid permeable to liquid, the solid substantially filling the space defined by the electrodes and the inner wall of the tube and means for applying an electric field to the electrodes, so that in use, when the field is applied, liquid is induced to flow through the solid and hence along the tube.

The above described liquid supply means allows an even liquid flow at precise rates, using the same (electrical) energy source that is used to generate the droplets thus requiring no mechanical means of pressurizing the liquid. The entire unit may thus be powered by very small battery-driven voltage sources, or even by a hand-operated piezoelectric device such as a stack of PVdF film or barium titanate ceramic. The device may thus be made pocket-size.

The invention also extends to the conduit, retaining means and means for applying the electric field as described above for use with the solid as defined above.

When used herein ‘a comminution’ includes a liquid droplet spray.

When used herein ‘medicament’ includes proprietary medicines, pharmaceutical medicines and veterinary medicines.

When used herein, unless more specifically defined herein, ‘inhaled adminisaion’ includes administration to and via the upper respiratory tract, including the nasal mucosa, and the lower respiratory tract.

When used herein ‘electrically insulating’ relates to a level of electrical insulation sufficient to allow an electric field to be applied across the solid, wherein the field is sufficient to induce liquid flow; preferably it includes semi and fully insulating materials.

When used herein the terms ‘liquid permeable’ or ‘permeable to liquid’ as applied to, for example, the solid and electrodes relate to solid and electrodes which are intrinsically permeable to liquid or to solid or electrodes which can be rendered permeable by processes for example, in the case of the solid, granulation or powdering or, for the electrode, by forming into shapes which allow the passage of liquid, such as mesh shapes.

The liquid medicinal formulations for use in the device of the invention may be formulated according to conventional procedures, such as those disclosed in the US Pharmacopoeia, the European Pharmacopoeia, 2nd Edition, Martindale The Extra Pharmacopoeia, 29th Edition, Pharmaceutical Press and the Veterinary Pharmacopoeia The liquid cosmetic formulations for use in the device of the invention may be formulated according to conventional procedures such as those disclosed in Harry's Cosmeticology, 9th Edition, 1982,George Goodwin, London.

The invention may now be described, by way of example, with reference to the accompanying drawings.

COMMINUTION SITES

Figure 1:
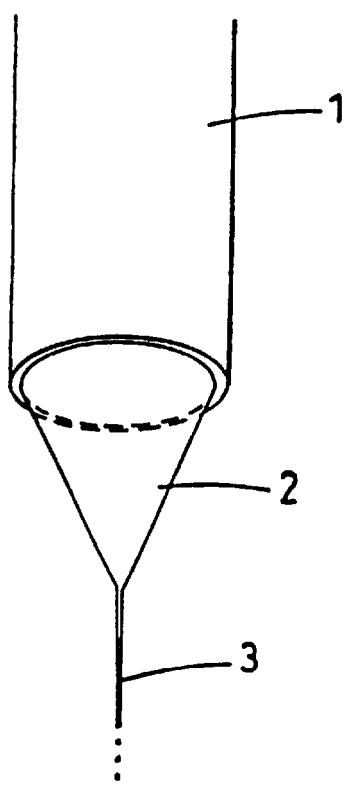
FIGS. 1 to 4 illustrate examples of comminution sites of the device of the invention.

FIG. 1 shows a thin-walled capillary tube (1), which may be made of conducting or semiconducting material and which may be electrically connected to a source of high-voltage direct-current, either directly or through the liquid. A single jet (3) is produced from a cusp (2) of liquid, both of which form naturally, according to the voltage and flow rate for a given liquid.

Figure 2:
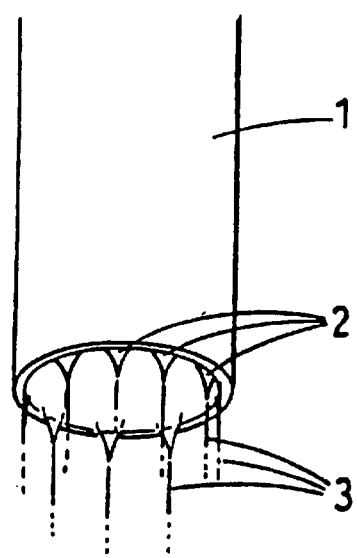

FIG. 2 shows a similar tube (1) used at a lower flow rate and voltage which are adjusted so as to produce multiple cusps (2) and jets (3) issuing from the region of the ends of the thin-walled tube (1).

Figure 3:
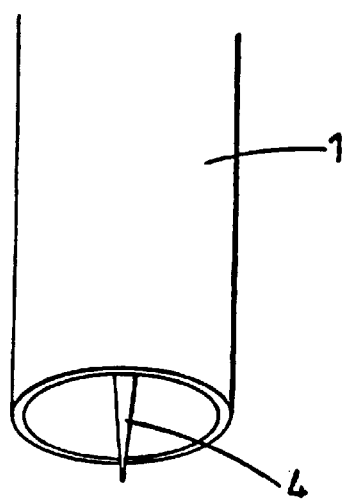

FIG. 3 shows a conducting or semiconducting cylinder (1) which may have a larger diameter than those shown in FIGS. 1 and 2. This nozzle has an inner-member, (4) which is approximately coaxial with the outer tube, (1).

Figure 4:
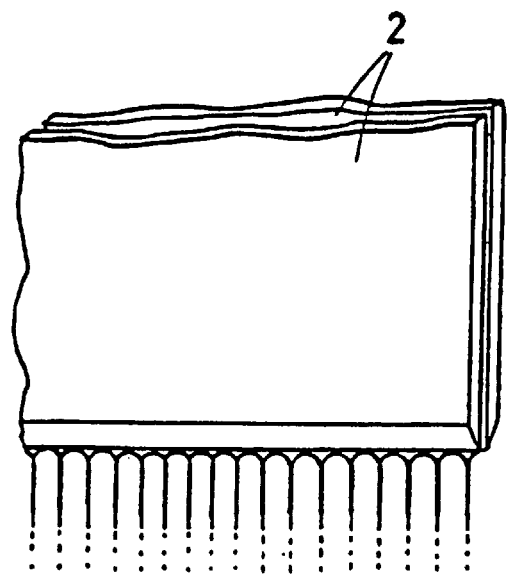

FIG. 4 shows a slot nozzle, formed between two parallel plates (2) having conducting, or semiconducting edges electrically connected to a high-voltage direct-current supply, from which the liquid emerges, forming cusps and jets when the voltage supply and liquid flow rates are suitably adjusted according to the type of liquid being sprayed For a given jet (and thus droplet) size, and a given liquid, this nozzle may enable a higher flow rate to be achieved than those in which a single cusp and jet are used.

Figure 5:
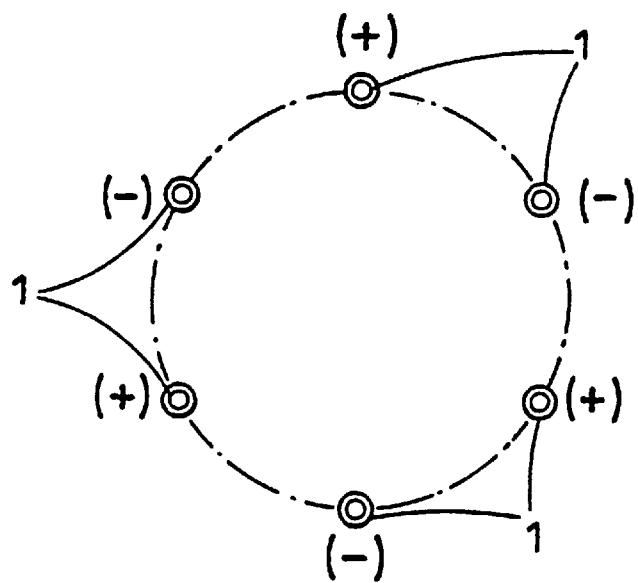
FIG. 5 is a plan view illustrating a multi-nozzle comminution site of the device of the invention.

FIG. 5, shows one example of an array of six nozzles (1) in a circular pattern, centrally mixing the sprays.

Liquid Supply Means

Figure 6:
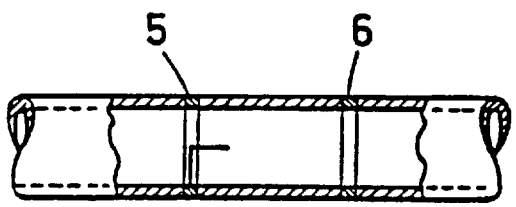
FIGS. 6 and 7 illustrate examples of the liquid supply means of the device of the invention.

An example of such a device is illustrated in FIG. 6 which shows an ion stream method, wherein a high voltage electrode (5) breaks up pairs of charge carriers within the liquid, thus neutralizing those of opposite polarity at the electrode, and leaving a large population of monionized like-polarity charge carriers which stream away from the high voltage electrode by coulombic force, thus moving the liquid in the direction of the counter electrode (6) by means of viscous drag. This pumping means requires that an electrode (5) is able to effectively inject like-polarity charge carriers into the liquid, close to the electrode (5). This may be effectively done by using a sharp-edged conducting or semiconducting surface, held at a sufficiently high potential to disrupt lightly bonded charge carriers or to ionize the liquid. Normally, it is only possible to establish a strong enough field for both creating unipolar charge carriers and pumping the liquid, when the liquid is of sufficient resistivity. Typically a resistivity of, say 10 (exp. 8) ohm meters, will pump at several millilitre per minute, with a head of up to one meter, at a voltage of 10 to 20 kilovolts, and a direct current of only a few microamperes. More conductive liquids will draw more current and will establish a weaker electric field. Thus highly conducting liquids, such as, say tap water may not establish a practicable drag pressure.

Figure 7:
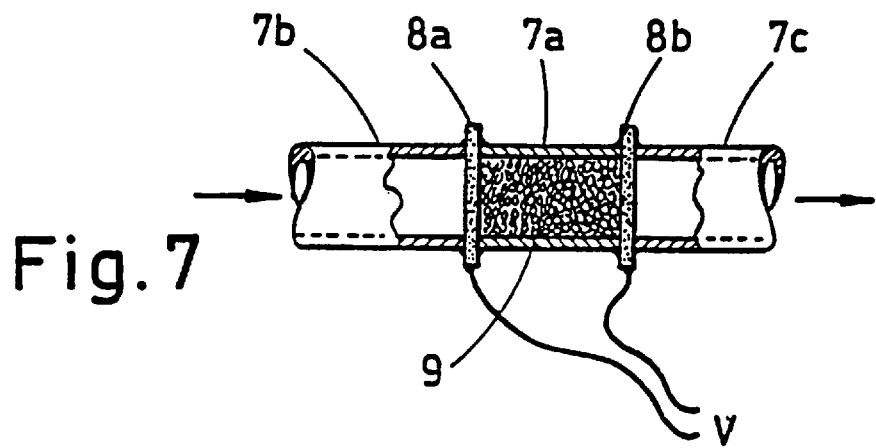

FIG. 7 shows an example of the novel pump of the invention in which a plastic tube (7a), 1.0 cm long, internal diameter 1.0 cm and 0.8 mm wall thickness has one of a pair of disc-shaped wire gauze electrodes (8a and 8b) bonded to each of its ends. A source of d.c. voltage is connected to each electrode. Liquid is supplied to and taken from tube (7a) by two further plastic tubes (7b and 7c) one of each being bonded to each wire gauze electrode (8a or 8b). Glass tube (7a) is filled with powdered silica (9). In operation, on applying a voltage to the electrodes (8a and 8b) a net forward force is exerted on the liquid which is interfaced with the silica (9) due to the presence of a double layer of charge at the solid-liquid interface. The polarity of the dc voltage is set so as to draw the liquid in the required direction, according to the polarity of the charge layer residing in the liquid at the liquid-solid interface. The pressure developed may be enhanced by using a solid of finer mesh size, thereby increasing n (see Scheme(I) above), with a maximized specific surface and with maximal zeta potential difference at the solid-liquid interface. Electrode voltages may be adjusted in accordance with the length of the current path between the two electrodes, so as to limit current flow to a desired value.

Using the device illustrated in FIG. 6 a flow rate of 0.03 mL sec$_{-1}$ was obtained with mineral oil of resistivity $10^7$ ohm m, relative permitivity ~2.5 and viscosity 22 centistokes with an applied voltage of 20 kV.

Electrical Charging Means

Figure 8:
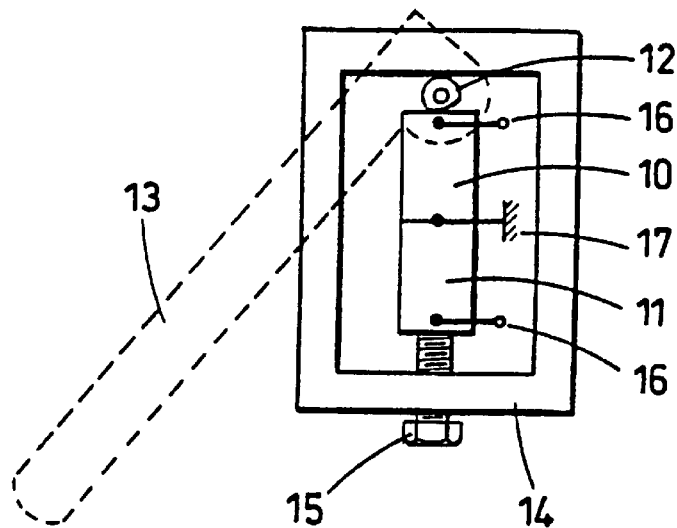
FIG. 8 is a schematic drawing illustrating an example of a charging means of the device of the invention.

An example of this is a piezo electric generator. FIG. 8 illustrates a pair of piezoelectric ceramic generators (10) (11) which may be easily squeezed by a cam (12) operated by a trigger-shaped lever (13). The entire assembly may be housed in a strong steel frame, (14), and the piezoelectric pair may be held tight by adjustment screw (15). The voltage terminals (16) are the two live electrodes for connection to the pumps and nozzles, whilst terminal (17) is earthed, say to the steel frame.

When the lever (13) is pulled inward, the two ceramic generators (10) and (11) will produce high voltages upon the terminals (16) placed at the end surfaces, which may be used to activate both the electrokinetic pumps and the nozzles Typical values of charge from say a barium titanate ceramic of about 1.0 cm length and 1.0 sq cm surface area would be 1.0 or 2.0 microcoulomb per squeeze, of either positive or negative polarity. Upon release of the squeezing pressure, a similar charge will flow in the opposite direction. A typical voltage would be say 5,000 to 10,000 volts. Thus, pumping and atomizing may both be achieved by hand operation of a single pair of piezoelectric generators at appropriate voltages, say 5,000 volts, and sufficient currents, say 2.0 microcoulombs per second (2.0 microamperes).

The piezoelectric material may be chosen from several types, such as barium titanate ceramic, or pvdf polymers, which generate significant high-voltage electric charge displacement upon being pressurized. The choice and capacity may be so chosen as to offer control of the degree of pumping and/or atomization when operated. The liquid flow induction, and the nozzle atomization will occur when the piezo electric generators are squeezed, and again (with opposite polarity) when the piezo electric generators are released from pressure. The device is arranged so that when squeezed, and when released the pumps and nozzles will operate without alteration of flow rate or droplet size. Only polarity will change (reverse) in the two modes of operation arising from pressure and release of pressure. This will maintain constant flow and droplet generation, and mixing of species and/or charge-to-mass ratio adjustment of the sprays, during the active modes of pressure, and release of pressure.

Figure 9:
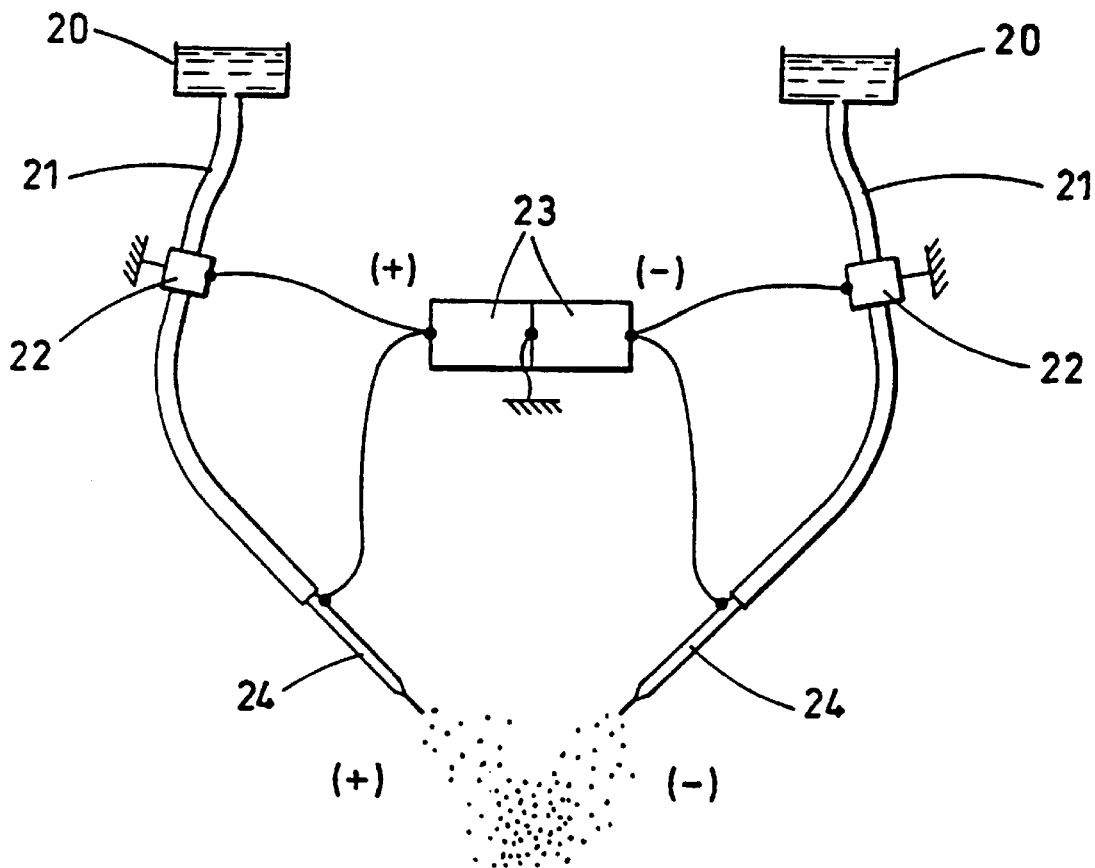
FIGS. 9 and 10 are schematic drawings each illustrating an example of a device of the invention.

Particular examples of the dispenser of the invention are illustrated below:

FIG. 9 shows a dispenser of the invention, in which liquid in each of two reservoirs (20) is caused to flow along suitable conduit, say polyethelene tubing (21) into two electrokinetic pumps (22), say by gravity feed. The two piezoelectic generators (23) are then squeezed so that a high voltage charge is induced at the two faces of the piezoelectric materials. These high voltages will then appear at the terminals of the pumps (22), which are electrically connected to the piezoelectric material by wire conductors.

At the same time, these high voltages will appear at the two conducting, or semi-conducting, capillary-tube nozzles (24). Thus, when the two liquids reach the two nozzles, the liquids will emerge from the nozzles as comminuted droplets with electrical charges of opposing polarity. The droplets will then be attracted to each other by electric field forces, and will tend to mix vigorously.

The value of droplet charge on each of the two streams of droplets may be independently adjusted to produce the optimum residual value by one or more of several means: the size, shape, ancvor materials of the two piezoclectrc materials may be set to give differing values of voltage and charge; the two liquid flow rates may also be adjusted, either by suitable design of the two electrokinetic pumps, or by differing values of piezoelectric voltage applied to the two pumps thus directly influencing droplet charge for a given voltage and nozzle design; and the droplet size and charge of the two liquids may be independently adjusted by the formulations of the two liquids, especially by adjustment of the liquid resistivities.

Figure 10:
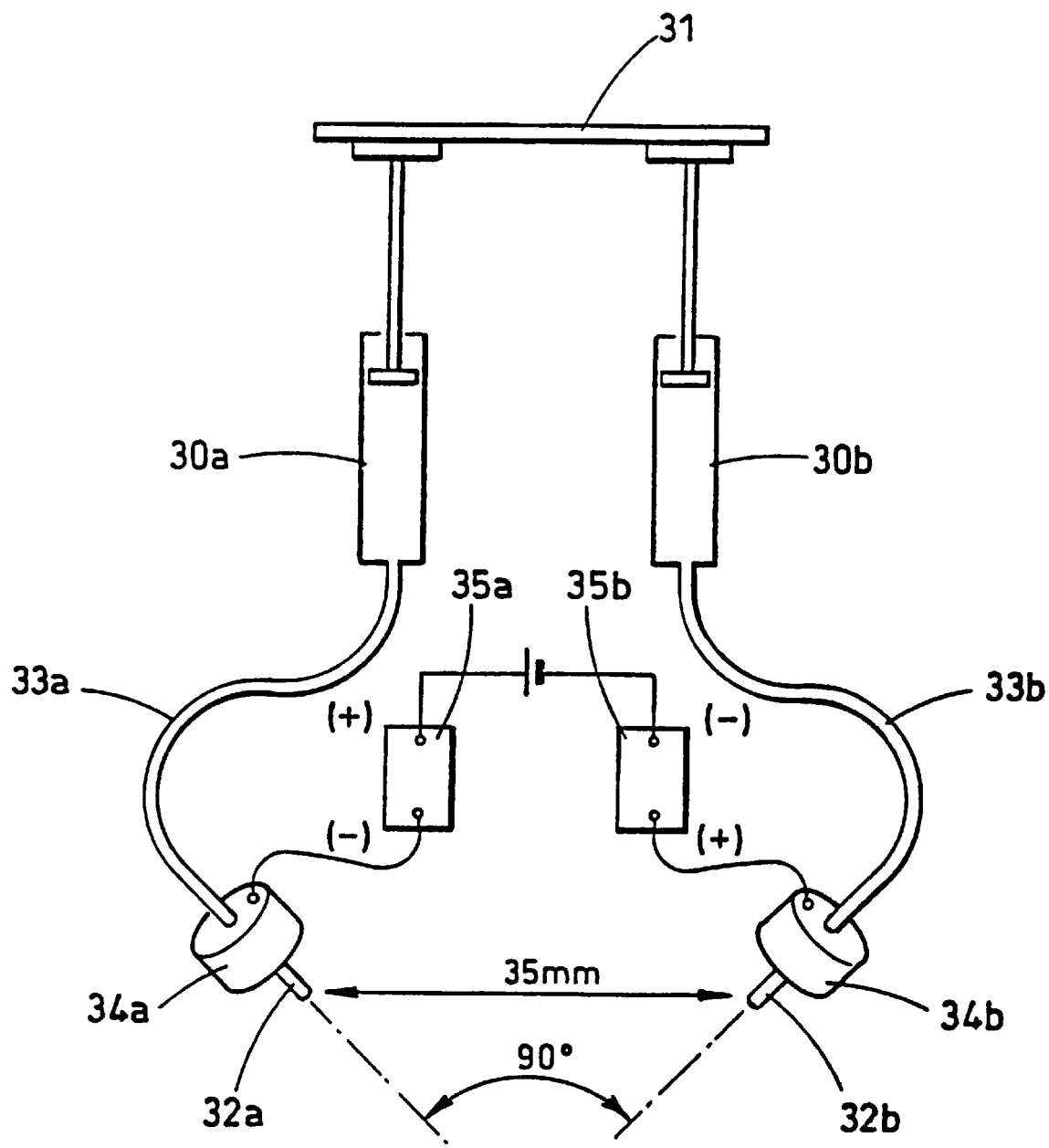

A second example of the dispenser of the invention is illustrated in FIG. 10: Two identical syringes (30a and 30b) are actuated by a rigid plate (31), the plate being attached to a motor drive unit. Two identical capillary nozzles (32a and 32b) each with internal diameters of 05 mm are each interconnected with one of the syringes (30a or 30b) by one of a pair of flexible tubes (33a and 33b). Each nozzle (32a and 32b) is fixed in a non-conducting mounting (34a or 34b respectively) so as to define an angle of approximately 90° with each other. One nozzle (32a) is attached to a high voltage source (35a) of (+) 6.7 kilovolts and the other nozzle (32b) is attached to a high voltage source (35b) of (−) 6.7 kilovolts.

In one particular experiment using the above described device, the flow rates of liquid (a mixture of 80% ethanol and 20% polyethylene glycol) from each syringe was adjusted to 1.0 μL/sec. The nozzles were attached to the high voltage sources of (+) and (−) 6.7 kVolts respectively. The two spray clouds were observed to mix virtually completely to provide an clectricay neutral spray.

I claim:

1. A method of providing droplets for delivery to the respiratory tract, which method comprises:
   supplying liquid along a first pipe to a first outlet for directing liquid into a mixing zone;
   supplying liquid along a second pipe to a second outlet for directing liquid lnto the mixing zone;
   subjecting liquid issuing from the first outlet to a first electrical potential causing the liquid to form a first comminution of droplets of one polarity; and
   subjecting liquid issuing from the second outlet to a second electrical potential causing the liquid to form a second comminution of droplets of a polarity opposite to the one polarity which droplets mix in the mixing zone with the droplets of the first comminution to for a mixed comminution for delivery to the respiratory tract.

2. A mthod of providing droplets for delivery to the respiratory tract, which method comprises:
   supplying liquid along a first pipe to a first outlet for directing liquid into a mixing zone;
   supplying liquid along a second pipe to a second outlet for directing liquid into the mixing zone;
   subjecting liquid issuing from the first outlet to a first electrical potential causing the liquid to form a first comminution of droplets of one polarity; and
   subjecting liquid issuing from the second outlet to a second electrical potential causing the liquid to form a second comminution of droplets of a polarity opposite to the one polarity which droplets mix in the mixing zone with the droplets of the first comminution to form a mixed comminution having droplets with diameters in the range of from about 10 micrometres to 20 microratres which is delivered to the respiratory tract.

3. A method according to claim 1 or 2 which comprises regulating the charge on the mixed comminution so that the overall charge of the mixed comminution is negative, positive or zero.

4. A method according to claimp or 1 or 2, which comprises supplying the liquids such that the mixed comminution has no overall charge.

5. A method according to claim 1 or 2, which comprises selecting the first and second electrical potentials such that the mixed comminution has an overall charge.

6. A method according to claim 1 or 2, which comprises selecting the first and second electrical potentials such that the mixed comminution has no overall charge.

7. A method according to claim 1 or 2, wherein the droplets of the mixed comminution have a diameter in the range of 0.1 to 25 microns.

8. A method according to claim 1 or 2 for providing droplets for delivery to the lower respiratory tract, wherein the droplets of the mixed comminution have a diameter in the range of from 0.1 to 10 microns.

9. A method according to claim 1 or 2 for providing droplets for delivery to the upper respiratory tract, wherein the droplets of the mixed comminution have a diameter in the range of 10 to 25 microns.

10. A method according to claim 1 or 2, which comprises supplying the liquids such that the mixed comminution has an overall charge.

11. A device for comminuting liquid, comprising:
   a first reservoir;
   a first pipe having a first outlet;
   a first pump for pumping liquid along the first pipe;

a second reservoir;

a second pipe having a second outlet;

a second pump for pumping liquid along the second pipe; and a voltage generator for activating the first and second pumps and for subjecting liquid issuing from the first outlet to an electrical potential to form a first comminution of one polarity and for subjecting liquid issuing from the second outlet to an electrical potential to form a comminution of a polarity opposite to the one polarity which mixes vigorously with the first comminution.

12. A device for comminuting liquid comprising:

a first liquid supplier having a first liquid outlet;

a second liquid supplier having a second liquid outlet with the first and second liquid outlets being angled towards one another;

a first electrohydrodynamic comminuter for subjecting liquid issuing from the first outlet to an electrical potential to cause the liquid to be comminuted to form a first comminution of one polarity; and a second electrohydrodynamic comminuter for subjecting liquid issuing from the second outlet to an electrical potential to cause the liquid to be comminuted to form a second comminution of a polarity opposite to said one polarity which mixes with the first comminution.

13. A device according to claim 11 or 12, wherein the first and second electrohydrodynamic comminuters comprise a piezoelectric generator for generating the electrical potentials.

14. A device according to claim 11 or 12, further comprising a regulator for regulating the electrical charge on the first and second comminutions so that the comminutions when mixed have a residual positive or negative charge.

15. A device according to claim 14, wherein the regulator is arranged to regulate the liquid flow rate along the first and second pipes.

16. A device according to claim 14, wherein the regulator is arranged to regulate the electrical potentials to which liquid issuing from the first and second outlets is subjected.

17. A device for comminuting liquid comprising:

a first liquid supplier having a first liquid outlet;

a second liquid supplier having a second liquid outlet;

first and second pumps for pumping liquid along the first and second pipes, each pump comprising an electrically insulating conduit enclosing an electrically insulating solid permeable to the liquid, a retainer for retaining the solid within the conduit and electrodes for applying an electric field across the solids for forming a double layer of charge at a solid-liquid interface within the solid to produce a net force for inducing liquid to flow through the solid and hence along the conduit;

a first electrohydrodynamic comminuter for subjecting liquid issuing from the first outlet to an electrical potential to cause the liquid to be comminuted to form a first comminution of one polarity; and a second electrohydrodynamic comminuter for subjecting liquid issuing from the second outlet to an electrical potential to cause the liquid to be comminuted to form a second coiminution of a polarity opposite to said one polarity which mixes with the first comminution.

18. A device according to claim 11, 12 or 17, which comprises a liquid supply regulator operable to control the supply of liquid such that the mixed comminution has no overall charge.

19. A device according to claim 11, 12 or 17, which comprises an electrical potential regulator for regulating the first and second electrical potentials such that the mixed comminution has an overall charge.

20. A device according to claim 11, 12 or 17, which comprises an electrical potential regulator for regulating the first and second electrical potentials such that the mixed comminution has no overall charge.

21. A device according to claim 11, 12 or 17, which comprises a liquid supply regulator operable to control the supply of liquid such that the mixed comminution has an overall charge.

22. A device according to claim 17, wherein the electrodes are constructed from one of wire gaure and electrically conducting titanium oxide.

23. A device according to claim 17 or 22, wherein the electrically insulated solid is a powder.

24. A device according to claim 17 or 22, wherein the electrically insulating solid is selected from the group consisting of powdered ceramic, powdered silica, powdered plastic, clay, fibrous ceramic and polymer fibres.

25. A device according to claim 21, which comprises a regulator operable to regulate the charge on the mixed comminution so that the overall charge of the mixed comminution is negative, positive or zero.

26. An inhaler comprising:

a first reservoir for liquid;

a first pipe coupled to the first reservoir and having a first outlet;

a second reservoir for liquid;

a second pipe couoled to the second reservoir and having a second outlet;

a first electrohydrodynamic comminuter for subjecting liquid issuing from the first outlet to an electrical potential to cause the liquid to form a first comminution of one polarity;

a second electrohydrodynamic comminuter for causing liquid issuing from the second outlet to form a second comminution of a polarity opposite to the one polarity; and a mixing zone into which the first and secord cowminutions are delivered whereby a mixed comminution for delivery to the respiratory tract of a user is formed.

27. An inhaler comprising:

a first liquid supplier having a first liquid outlet;

a second liquid supplier having a second liquid outlet;

a first electrohydrodynamic comminuter for subjecting liquid issuing from the first outlet to an electrical potential to cause the liquid to be coinuted to form a first comminution;

a second electrohydrodynamic comminuter for subjecting liquid issuing from the second outlet to an electrical potential to cause the liquid to be comminuted to form a second comilnution, the first and second outlets being angled towards one another so as to direct the first and second comminutions towards one another to cause substantial admixing of the first and second comminutions.

28. A device for comminuting liquid, comprising:

a first liquid supplier having a first liquid outlet;

a second liquid supplier having a second liquid outlet;

a first electrohydrodynamic comminuter for subjecting liquid issuing from the first outlet to an electrical potential to cause the liquid to be comminuted to form a first comminution;

a second electrohydrodynamic comminuter for subjecting liquid issuing from the second outlet to an electrical potential to cause the liquid to be conminuted to form a second conminution, the first and second outlets being angled towards one anwther so as to direct the first and second comminutions toward one another to cause substantial admixing of the first and second comminutions.

29. A pocket sized dispenser, comprising:

a first liquid supplier having a first liquid outlet;

a second liquid supplier having a second liquid outlet;

a first electrohydrodynamic comminuter for sujecting liquid issuing from the first outlet to an electrical potential to cause the liquid to be comminuted to form a first comminution;

a second electrohydrodynamic comminuter for subjecting liquid issuing from the second outlet to an electrical potential to cause the liquid to be comminuted to form a second comminution; and a mixing zone for receiving and mixing the first and second comminutions.

30. A pocket-sized dispenser comprising means for supplying liquid to first and second outlets; a first electrohydrodynamic comminution means for subjecting liquid issuing from the first outlet to an electrical potential to cause the liquid to be comminuted to form a comminution of one polarity; and a second electrohydrodynamic comminution means for subjecting liquid issuing from the second outlet to an electrical potential to cause the liquid to be comminuted to form a comminution of the opposite polarity, the first and second electrohydrodynamic comminution means therefore giving rise to formation of two opposite polarity cominutions and being arranged so as to cause substantial admixing of the two opposite polarity comminutions.

31. A medicament delivery device comprising:

a first liquid reservoir containing a medicament;

a second liquid reservoir containing deionised water;

a first liquid supply pipe coupled to the first liquid reservoir;

a second liquid supply pipe coupled to the second liquid reservoir;

a first electrohydrodynamic comminuter for subjecting liquid issuing from the first outlet to a first electrical potential to provide a first comminution with an average charge of +/− Qa; and a second electrohydrodynamic comminuter for subjecting liquid issuing from the second outlet to a second electrical potential to provide a second comminution with an average charge of −/+ Qb which mixes with the first comminution to provide a mixed commninution having an overall average positive or negative charge having a value equal to the modulus of (Qa−Qb).

32. A device for comminuting liquid, comprising:

a first liquid supplier having a first liquid outlet;

a second liquid supplier having a second liquid outlet;

a first electrohydrodynamic comminuter for subjecting liquid issuing from the first outlet to an electrical potential to cause the liquid to be commented to form a second comminution;

a second electrohydrodynamic comminuter for subjecting liquid issuing from the second outlet to an electrical potential to cause the liquid to be comminuted to form a second comminution;

a mixing zone for receiving and mixing the first and second comminutions, the rate of flow of liquid provided by the first and second liquid suppliers and the electrical potentials to which the liquid is subjected by the first and second electrohydrodynamic comminuters being controlled to provide droplets having a diameter in the range of from 0.1 to 25 micrometers.

33. A device according to claim 32, wherein the rate of flow of liquid and the electrical potentials are controlled to provide droplets having a diameter in the range 0.5 to 10 micrometer.

34. A device for comminuting liquid comprising means for supplying liquid to first and second outlets;

a first electrohydrodynamic comminution means for subjecting liquid issuing from the first outlet to an electrical potential to cause the liquid to be comminuted to form a comminution of one polarity; and a second electrohydrodynamic comminution means for subjecting liquid issuing from the second outlet to an electrical potential to cause the liquid to be comminuted to form a comminution of the opposite polarity, the first and second electrohydrodynamnic comminution means therefore giving rise to formation oftwo opposite polarity comminutions and being arranged so as to cause substantial admixing of the two opposite polarity comminutions, and means for controlling the rate of flow of liquid provided by the liquid supply means and the electrical potentials to which liquid is subjected by the first and second electrohydrodynamic comminution means to provide droplets having a diameter in the range 0.1 to 25 micrometers.

35. A device according to claim 34, wherein the controlling means is arranged to control the droplet diameter to be in the range 0.5 to 10 micrometers.

36. A device according to claim 34, wherein the controlling means is arranged to control the droplet size to be in the range 10 to 20 micrometers.

37. A method of reacting components, which method comprises:

supplying liquid containing a first reactive component to a first liquid outlet;

supplying liquid containing a second reactive component to a second liquid outlet;

subjecting liquid issuing from the first outlet to a first electrical potential causing the liquid to form a first comminution of droplets of one polarity; and subjecting liquid issuing from the second outlet to a second electrical potential causing the liquid to form a second comminution of droplets of a polarity opposite to the one polarity whereby the opposite polarity comrminutions mix and the reactive components of oppositely charged droplets chemically react immediately upon mixing of the opposite polarity comminutions.

38. A method according to claim 37, which comprises controlling the rate of flow of the liquids and the electrical potentials to provide droplets having a diameter in the range 0.1 to 25 micrometers.

39. A method accordingto claim 37, which comprises controlling the rate of flow of liquid and the electrical potentials so as to provide droplets having a diameter in the range 0.5 to 10 micrometers.

40. A method according to claim 37, which comprises controlling the rate of flow of liquid and the electrical potentials to provide droplets having a diameter in the range of 10 to 20 micrometers.

41. A method of mixing liquids by droplet coalescence, which method comprises:

supplying liquid containing a first chemical to a first liquid outlet;

supplying liquid containing a second chemical to a second liquid outlet;

subjecting liquid issuing from the first outlet to a first electrical potential causing the liquid to form a first comminution of droplets of one polarity; and subject liquid issuing from the second outlet to a second electrical potential causing the liquid to form a second comminution of droplets of a polarity opposite to the one polarity whereby the opposite polarity comminutions mix and the first and second chemicals of the oppositely charged droplets chemically react upon mixing of the opposite polarity comminution.

42. A method according to claim 41, which comprises controlling the rate of flow of the liquids and the electrical potentials to provide droplets having a diameter in the range 0.1 to 25 micrometers.

43. A method according to claim 41, which comprises controlling the rate of flow of liquid and the electrical potentials so as to provide droplets having a diameter in the range 0.5 to 10 micrometers.

44. A method according to claim 41, which comprises controlling the rate of flow of liquid and the electrical potentials to provide droplets having a diameter in the range of 10 to 20 micrometers.

* * * * *